(12) United States Patent
Johnson et al.

(10) Patent No.: US 11,135,057 B2
(45) Date of Patent: Oct. 5, 2021

(54) DUAL-WIREFORM LIMITED EXPANSION HEART VALVES

(71) Applicant: Edwards Lifesciences Corporation, Irvine, CA (US)

(72) Inventors: Derrick Johnson, Orange, CA (US); Michael C. Murad, Lake Mathews, CA (US); Steven M. Ford, Laguna Beach, CA (US); Rodolfo Rodriguez, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 59 days.

(21) Appl. No.: 16/721,727

(22) Filed: Dec. 19, 2019

(65) Prior Publication Data

US 2020/0121456 A1 Apr. 23, 2020

Related U.S. Application Data

(63) Continuation of application No. PCT/US2018/038527, filed on Jun. 20, 2018.

(60) Provisional application No. 62/523,157, filed on Jun. 21, 2017.

(51) Int. Cl.
*A61F 2/24* (2006.01)

(52) U.S. Cl.
CPC .............. *A61F 2/2418* (2013.01); *A61F 2/24* (2013.01); *A61F 2230/006* (2013.01)

(58) Field of Classification Search
CPC ............ A61F 2/2418; A61F 2220/0075; A61F 2/2412; A61F 2210/0014; A61F 2/2409; A61F 2/2445; A61F 2220/0008; A61F 2250/0039; A61F 2250/006; A61F 2/2442; A61F 2/24; A61F 2/89; A61F 2230/0006; A61F 2230/008; A61F 2/915; A61F 2230/006

See application file for complete search history.

(56) References Cited

U.S. PATENT DOCUMENTS

| | | |
|---|---|---|
| 3,143,742 A | 8/1964 | Cromie |
| 3,320,972 A | 5/1967 | High et al. |
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |

(Continued)

FOREIGN PATENT DOCUMENTS

| | | |
|---|---|---|
| EP | 0125393 A1 | 11/1984 |
| EP | 0143246 A2 | 6/1985 |

(Continued)

*Primary Examiner* — Ann Schillinger
(74) *Attorney, Agent, or Firm* — Guy Cumberbatch

(57) ABSTRACT

A prosthetic heart valve configured to replace a native heart valve and having a support frame configured to be reshaped into an expanded form in order to receive and/or support an expandable prosthetic heart valve therein. A dual-wireform support frame including an upper and a lower wireform permits expansion of the valve by one or two valve sizes, for example, with a 2-mm gap between each valve size. The lower wireform has a relatively shallow undulation so that it may stretch apart by a small amount and then prevent further expansion of the valve.

20 Claims, 4 Drawing Sheets

(56) References Cited

U.S. PATENT DOCUMENTS

| | | |
|---|---|---|
| 3,997,923 A | 12/1976 | Possis |
| 4,035,849 A | 7/1977 | Angell et al. |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichert et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,487,760 A | 1/1996 | Villafana |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,762 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,409,674 B1 | 6/2002 | Brockway et al. |
| 6,425,916 B1 | 7/2002 | Garrison et al. |
| 6,440,164 B1 | 8/2002 | DiMatteo et al. |
| 6,442,413 B1 | 8/2002 | Silver |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,645,143 B2 | 11/2003 | VanTassel et al. |
| 6,652,464 B2 | 11/2003 | Schwartz et al. |
| 6,652,578 B2 | 11/2003 | Bailey et al. |
| 6,675,049 B2 | 1/2004 | Thompson et al. |
| 6,682,559 B2 | 1/2004 | Myers et al. |
| 6,685,739 B2 | 2/2004 | DiMatteo et al. |
| 6,730,118 B2 | 5/2004 | Spenser et al. |

(56) References Cited

U.S. PATENT DOCUMENTS

| | | |
|---|---|---|
| 6,733,525 B2 | 5/2004 | Yang et al. |
| 6,741,885 B1 | 5/2004 | Park et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,795,732 B2 | 9/2004 | Stadler et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,895,265 B2 | 5/2005 | Silver |
| 6,908,481 B2 | 6/2005 | Cribier |
| 6,939,365 B1 | 9/2005 | Fogarty et al. |
| 7,011,681 B2 | 3/2006 | Vesely |
| 7,025,760 B2 | 4/2006 | Gabbay |
| 7,033,322 B2 | 4/2006 | Silver |
| 7,052,466 B2 | 5/2006 | Scheiner et al. |
| 7,070,616 B2 | 7/2006 | Majercak et al. |
| 7,082,330 B2 | 7/2006 | Stadler et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,416,530 B2 | 8/2008 | Turner et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,621,878 B2 | 11/2009 | Ericson et al. |
| 7,871,435 B2 * | 1/2011 | Carpentier ............ A61F 2/2418 623/2.15 |
| 7,916,013 B2 | 3/2011 | Stevenson |
| 7,998,151 B2 | 8/2011 | St. Goar et al. |
| 8,066,650 B2 | 11/2011 | Lee et al. |
| 8,248,232 B2 | 8/2012 | Stevenson et al. |
| 8,253,555 B2 | 8/2012 | Stevenson et al. |
| 8,340,750 B2 | 12/2012 | Prakash et al. |
| 8,401,659 B2 | 3/2013 | Von Arx et al. |
| 8,529,474 B2 | 9/2013 | Gupta et al. |
| 8,613,765 B2 * | 12/2013 | Bonhoeffer ............ A61F 2/2412 623/2.17 |
| 8,622,936 B2 | 1/2014 | Schenberger et al. |
| 9,101,264 B2 | 8/2015 | Acquista |
| 9,101,281 B2 | 8/2015 | Reinert et al. |
| 10,456,246 B2 * | 10/2019 | Conklin ................ A61F 2/2409 |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0010296 A1 | 1/2004 | Swanson et al. |
| 2004/0019374 A1 | 1/2004 | Hojeibane et al. |
| 2004/0027306 A1 | 2/2004 | Amundson et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |

(56) References Cited

U.S. PATENT DOCUMENTS

| | | |
|---|---|---|
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwarnmenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0046040 A1 | 2/2008 | Denker et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0192591 A1 | 7/2009 | Ryan et al. |
| 2009/0192599 A1 | 7/2009 | Lane et al. |
| 2010/0049313 A1 | 2/2010 | Alon et al. |
| 2010/0145438 A1 | 6/2010 | Barone |
| 2010/0256723 A1 | 10/2010 | Murray |
| 2012/0078357 A1 | 3/2012 | Conklin |
| 2012/0123284 A1 | 5/2012 | Kheradvar |
| 2012/0239143 A1 | 9/2012 | Rankin et al. |
| 2012/0296382 A1 | 11/2012 | Shuros et al. |
| 2013/0144379 A1 | 6/2013 | Najafi et al. |
| 2014/0128964 A1 | 5/2014 | Delaloye |
| 2014/0188219 A1* | 7/2014 | Conklin ............ A61F 2/2445 623/2.17 |
| 2014/0188221 A1* | 7/2014 | Chung ............... A61F 2/2418 623/2.18 |
| 2014/0364707 A1 | 12/2014 | Kintz et al. |
| 2015/0045635 A1 | 2/2015 | Tankiewicz et al. |
| 2015/0088250 A1* | 3/2015 | Zeng ................. A61F 2/2409 623/2.12 |
| 2015/0366664 A1* | 12/2015 | Guttenberg ........ A61F 2/2412 623/2.17 |
| 2016/0045316 A1 | 2/2016 | Braido et al. |
| 2016/0158013 A1* | 6/2016 | Carpentier ........ A61F 2/2403 623/2.37 |
| 2016/0296331 A1* | 10/2016 | Chung ............... A61F 2/2445 |
| 2017/0000603 A1* | 1/2017 | Conklin ............ A61F 2/2409 |
| 2017/0071732 A1* | 3/2017 | Conklin ............ A61F 2/2418 |
| 2019/0321170 A1 | 10/2019 | Green et al. |

FOREIGN PATENT DOCUMENTS

| | | |
|---|---|---|
| SU | 1116573 A1 | 7/1985 |
| SU | 1697790 A1 | 12/1991 |
| WO | 9213502 A1 | 8/1992 |
| WO | 9742871 A1 | 11/1997 |

* cited by examiner

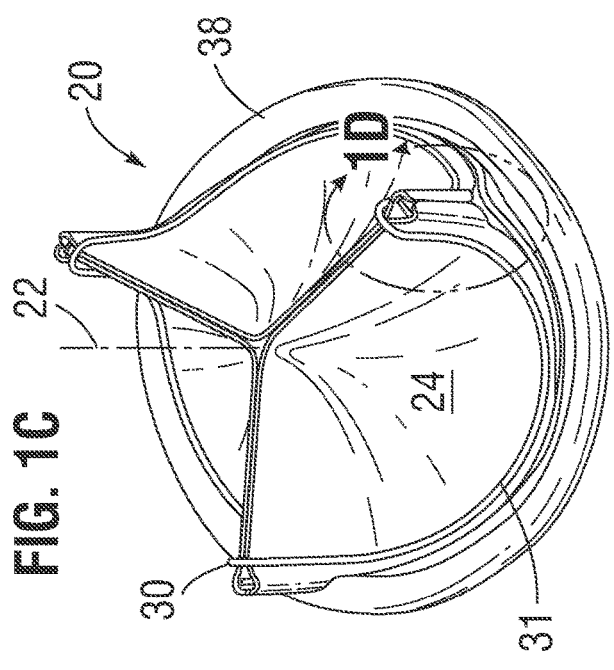
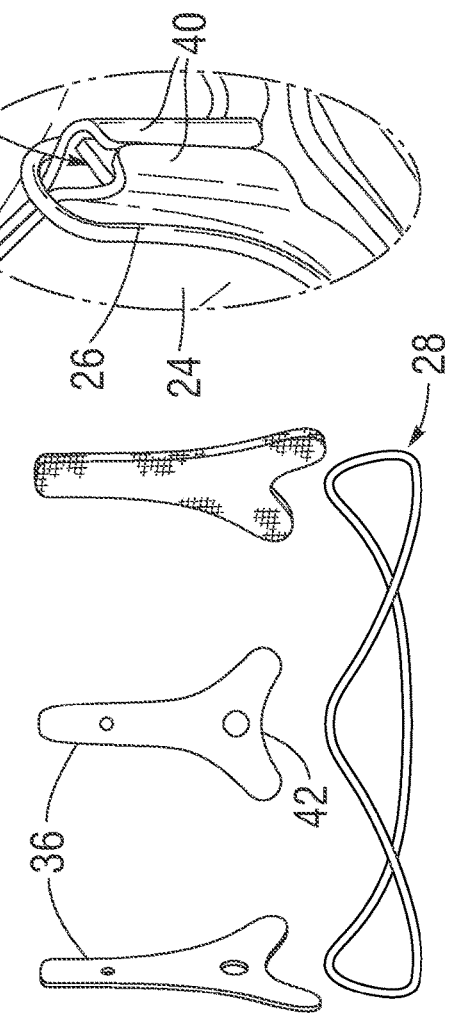
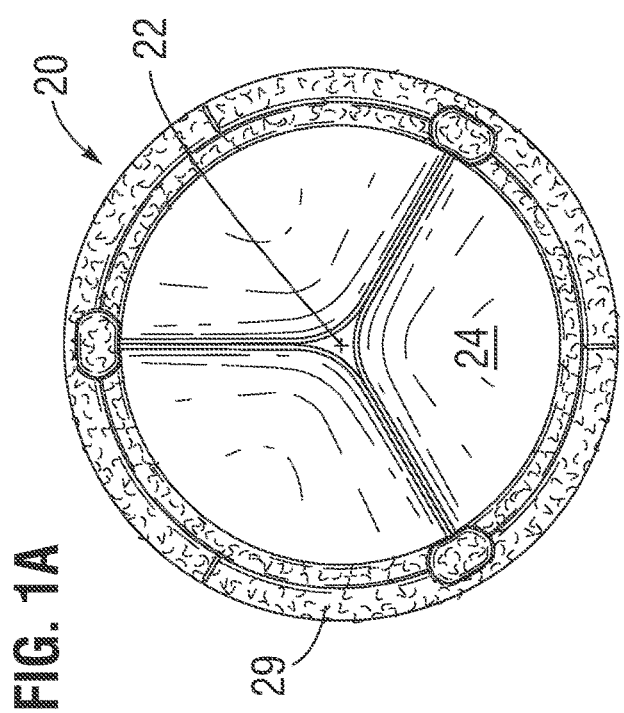
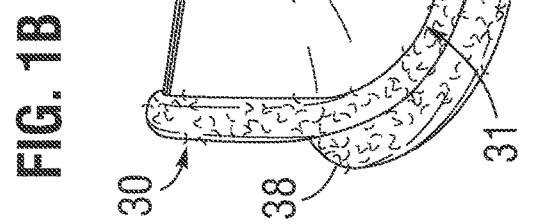

DUAL-WIREFORM LIMITED EXPANSION HEART VALVES

This application is a continuation of International Patent Application No. PCT/US2018/038527, filed Jun. 20, 2018, which claims the benefit of U.S. Patent Application No. 62/523,157, filed Jun. 21, 2017, the entire disclosures all of which are incorporated by reference for all purposes.

The present disclosure relates to a heart valve for heart valve replacement, and more particularly to modifications to the construction of a surgical heart valve to enable receiving an expandable prosthetic heart valve therein and to expand to a limited degree.

The heart is a hollow muscular organ having four pumping chambers separated by four heart valves: aortic, mitral (or bicuspid), tricuspid, and pulmonary. Each heart valve is comprised of a dense fibrous ring known as the annulus, and leaflets or cusps attached to the annulus.

Heart valve disease is a widespread condition in which one or more of the valves of the heart fails to function properly. In a traditional valve replacement operation, the damaged leaflets are typically excised and the annulus sculpted to receive a replacement prosthetic valve.

In tissue-type valves, a whole xenograft valve (e.g., porcine) or a plurality of xenograft leaflets (e.g., bovine pericardium) can provide fluid occluding surfaces. Synthetic leaflets have been proposed, and thus the term "flexible leaflet valve" refers to both natural and artificial "tissue-type" valves. In a typical tissue-type valve, two or more flexible leaflets are mounted within a peripheral support structure that usually includes posts or commissures extending in the outflow direction to mimic natural fibrous commissures in the native annulus. The metallic or polymeric "support frame," sometimes called a "wireform" or "stent," has a plurality (typically three) of large radius cusps supporting the cusp region of the flexible leaflets (e.g., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. Components of the valve are usually assembled with one or more biocompatible fabric (e.g., DACRON® polyethylene terephthalate) coverings, and a fabric-covered sewing ring is provided on the inflow end of the peripheral support structure.

Sometimes the need for complete valve replacement may arise after a patient has already had an earlier valve replacement for the same valve. For example, a prosthetic heart valve that was successfully implanted to replace a native valve may itself suffer damage and/or wear and tear many years after initially being implanted. Implanting a new prosthetic heart valve directly within a previously-implanted prosthetic heart valve (a so-called valve-in-valve procedure) may be impractical since traditional prosthetic heart valves may not be configured to easily receive such a valve-within-a-valve implantation in a manner which provides secure seating for the new valve while also having a large enough annulus within the new valve to support proper blood flow therethrough.

Some attention has been paid to the problem of implanting a new valve within an old valve. In particular, the following disclose various solutions for valve-in-valve systems: U.S. Patent Application Publication No. 2010/0076548 A1, filed Sep. 19, 2008; U.S. Pat. No. 8,613,765, filed Jul. 7, 2011; and International Patent Application Publication No. WO 2012/018779, filed Aug. 2, 2011. The entire disclosures of these publications are expressly incorporated herein by reference. Typically, the originally implanted heart valve is subjected to an outward dilatory force such as with an expanding balloon, until it expands to permit introduction of a new expandable valve within its orifice. The outward dilatory force from within the heart valve is typically substantially larger than forces associated with normal physiological cycling. The expansion may be done simultaneously with the new valve implantation.

Despite certain advances in valve-in-valve technology, there remains a need for a prosthetic heart valve that facilitates valve-in-valve procedures and simplifies manufacturing techniques.

Some embodiments provide a prosthetic heart valve configured to receive an expandable prosthetic heart valve, such as a catheter-deployed (transcatheter) prosthetic heart valve, therein. The prosthetic heart valve replaces a native heart valve and has a support frame configured to be reshaped into an expanded form in order to receive and/or support the expandable prosthetic heart valve therein. A dual-wireform support frame including an upper and a lower wireform permits expansion of the valve by one or two valve sizes, for example, with a 2-mm gap between each valve size. The expansion occurs upon application of an outward dilatory force from within the heart valve substantially larger than forces associated with normal physiological cycling. The lower wireform has a relatively shallow undulation so that it may stretch apart by a small amount and then prevent further expansion of the valve.

In a first aspect, the present application discloses a prosthetic heart valve adapted for post-implant expansion and having an inflow end and an outflow end. An upper wireform undulates around a central axis with three upstanding commissure posts extending in an outflow direction alternating with three arcuate inflow cusps, and a fabric covering around the entire upper wireform. A lower wireform undulates around the central axis with three truncated peaks extending in an outflow direction alternating with three arcuate inflow cusp sections, with a fabric covering around the entire lower wireform. The lower wireform is positioned axially below the upper wireform with the three truncated peaks being aligned under three upstanding commissure posts of the upper wireform, and wherein the truncated peaks have an axial height of between about 10-30% of the commissure posts. Three flexible leaflets having outer arcuate cusp edges attach between the inflow cusps of the upper wireform and the inflow cusp sections of the lower wireform. Outer tabs of the leaflets extend outward between the commissure posts of the upper wireform and the truncated peaks of the lower wireform and are secured to the fabric covering around the upper wireform, the flexible leaflets being configured to ensure one-way blood flow through the heart valve. The inflow cusps of the upper wireform and the inflow cusp sections of the lower wireform together define an implant circumference having a first diameter, wherein the upper and lower wireforms permit expansion of the heart valve from the first diameter to a second diameter no greater than 3 mm larger than the first diameter upon application of an outward dilatory force from within the heart valve substantially larger than forces associated with normal physiological cycling. Finally, the lower wireform has a shallow undulating shape that flattens out and prevents expansion of the heart valve beyond the second diameter The prosthetic heart valve of the first aspect may further include three fabric-covered inserts located above the truncated peaks of the lower wireform that extend upward radially outward of the commissure posts of the upper wireform, the leaflet tabs being also secured to the inserts.

Preferably, a lower end of each insert has an inverted Y-shape that closely matches a shape of the truncated peaks of the lower wireform.

The prosthetic heart valve of the first aspect may further include an annular sealing ring disposed outward of the inflow cusp sections of the lower wireform and being secured thereto, the annular sealing ring being suture permeable. In one embodiment, the lower wireform is embedded within the sealing ring.

The lower wireform may comprises a solid wire or a braided cable.

The prosthetic heart valve of the first aspect may further include an expandable frame attached to an inflow end of the heart valve and projecting therefrom in the inflow direction, the expandable frame having an upper undulating strut that extends around an entire periphery thereof and a plurality of lower struts. The undulating strut has a shape that closely follows the shape of the undulating lower wireform, wherein there are no lower struts below three peaks of the undulating strut to permit flattening out of the undulating strut upon application of an outward dilatory force from within the heart valve substantially larger than forces associated with normal physiological cycling.

In a second aspect, a prosthetic heart valve adapted for post-implant expansion and having an inflow end and an outflow end, comprises an upper wireform undulating around a central axis with three upstanding commissure posts extending in an outflow direction alternating with three arcuate inflow cusps, and a fabric covering around the entire upper wireform. An annular sealing ring is disposed outward of the inflow cusps of the upper wireform and is secured thereto, the annular sealing ring being suture permeable. A braided cable undulates around the central axis with three truncated peaks extending in an outflow direction alternating with three arcuate inflow cusp sections, the braided cable being embedded within the sealing ring and the three truncated peaks being aligned under three upstanding commissure posts. Three flexible leaflets having outer arcuate cusp edges attach between the inflow cusps of the upper wireform and the sealing ring. Outer tabs of the leaflets extend outward between the commissure posts of the upper wireform and are secured to the fabric covering around the upper wireform, the flexible leaflets being configured to ensure one-way blood flow through the heart valve. The inflow cusps of the upper wireform and the inflow cusp sections of the braided cable together define an implant circumference having a first diameter, wherein the upper wireform and braided cable permit expansion of the heart valve from the first diameter to a second diameter no greater than 3 mm larger than the first diameter upon application of an outward dilatory force from within the heart valve substantially larger than forces associated with normal physiological cycling. Finally, the braided cable has a shallow undulating shape that flattens out and prevents expansion of the heart valve beyond the second diameter The prosthetic heart valve of the second aspect may further include three fabric-covered inserts located above the truncated peaks of the braided cable that extend upward radially outward of the commissure posts of the upper wireform, the leaflet tabs being also secured to the inserts. Lower ends of each insert may have an inverted Y-shape that closely matches a shape of the truncated peaks of the braided cable.

The braided cable may be joined together at free ends at a weld in one of the cusp sections, or at a crimp at one of the truncated peaks.

The prosthetic heart valve of the second aspect may further include an expandable frame attached to an inflow end of the heart valve and projecting therefrom in the inflow direction, the expandable frame having an upper undulating strut that extends around an entire periphery thereof and a plurality of lower struts. The undulating strut has a shape that closely follows the shape of the undulating lower wireform, wherein there are no lower struts below three peaks of the undulating strut to permit flattening out of the undulating strut upon application of an outward dilatory force from within the heart valve substantially larger than forces associated with normal physiological cycling.

Other features and advantages will become apparent from the following detailed description, taken in conjunction with the accompanying drawings that illustrate, by way of example, certain principles and examples.

FIGS. 1A-1E are a number of views of an exemplary prosthetic heart valve of the present invention having a dual wireform construction including an expansion limiting suture in place of inner structural bands;

Figure 3:
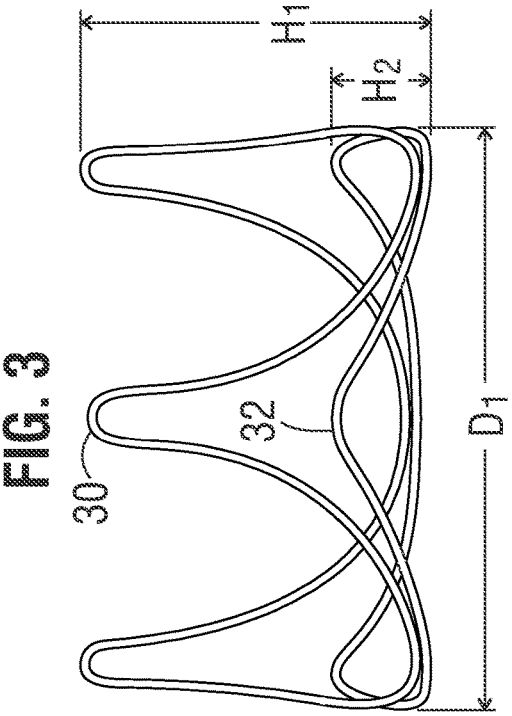
FIG. 3 is a view of the dual wireform assembly showing exemplary dimensions.

The prosthetic heart valves disclosed herein include a prosthetic valve member constructed similarly to embodiments of some commercially available surgical valves, with a relatively stable diameter that is not intended to be compressed or expanded during delivery and after implant when functioning as a one-way valve. The prosthetic heart valves described herein each include an internal (meaning incorporated into the valve member itself as opposed to being a supplemental element) structural stent or frame that is generally tubular in shape and that defines a flow orifice area through which blood flows from an inflow end to an outflow end. Alternatively, the shape of the internal stent can be oval, elliptical, D-shaped, irregular, or any other desired and functional shape. The valves include flexible leaflets that selectively open and close to allow for one-way fluid flow therethrough.

The present application discloses specific modifications to existing surgical valves that enable manufacturers to rapidly produce a valve that accommodates valve-in-valve (ViV) procedures. Specifically, the present application contemplates modifying certain components within existing surgical valve designs to enable post-implant expansion, which not only converts any proven surgical valve design for use in a ViV procedure, but it also reduces design and manufacturing work. Consequently, components of one popular surgical valve are described below to illustrate certain modifications thereto.

FIGS. 1A-1E are various views of an exemplary surgical prosthetic heart valve 20 oriented around a flow axis 22. The heart valve 20 comprises a plurality (typically three) of flexible leaflets 24 supported partly by an undulating upper wireform 26 as well as by a lower wireform 28. The upper wireform 26 and lower wireform 28 are visible in the figures, but are normally separately covered with a polyester fabric to facilitate assembly and reduce direct blood exposure after implant. The directions up and down are aligned along the flow axis 22 and generally correspond to flow directions, with the blood flowing up along the axis past the leaflets 24 in an outflow direction when the heart valve 20 is implanted.

Certain characteristics of the prosthetic heart valve 20 are common to a number of different prosthetic heart valves, such as pericardial heart valves manufactured by Edwards Lifesciences of Irvine, Calif. For example, the Edwards PERIMOUNT® heart valves that utilize pericardial leaflets 24 features a leaflet-supporting wireform such as the upper wireform 26, but also has an inner stent comprising a relatively non-expandable circular band structure. The exemplary heart valve 20 disclosed herein improves on the PERIMOUNT® heart valves by avoiding inner support structure which inhibits post-implant expansion.

Figure 2A:
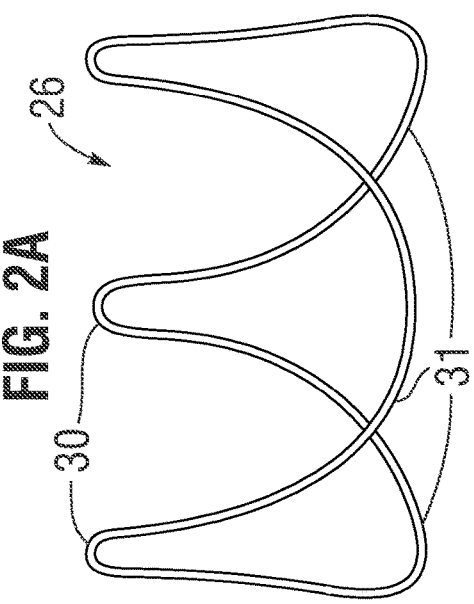
FIG. 2A is an elevational view of an upper wireform.
Figure 2B:
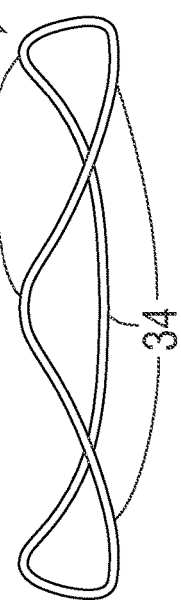
FIG. 2B is an elevational view of a lower platform.
Figure 2C:
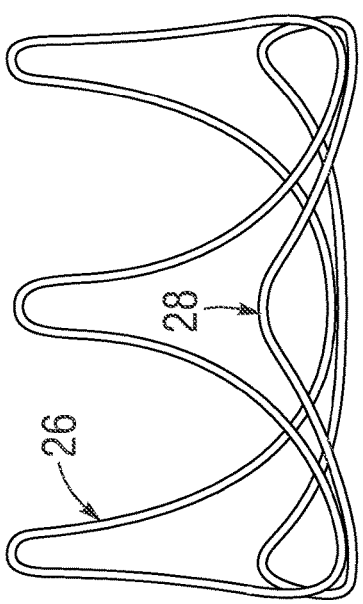
FIG. 2C is a schematic view showing the upper and lower wireforms in the positions they assume when assembled within a heart valve.

FIG. 2A is an elevational view of the upper wireform 26, FIG. 2B is an elevational view of a lower wireform 28, and FIG. 2C is a schematic view showing the upper and lower wireforms in the approximate positions they assume when assembled within the heart valve 20. The upper wireform 26 may be formed from a suitably elastic metal, such as a Co—Cr—Ni alloy like ELGILOY® alloy. The upper wireform 26 has a continuous undulating wire-like structure with (preferably) three upstanding commissure posts 30 in between three downwardly curved valleys typically termed cusps 31, as best seen in FIG. 1C. The wireform 26 forms narrow inverted "U" shapes at the commissure posts 30 that project in the outflow direction and define the farthest extent of the valve in that direction aside from fabric covering. This undulating band shape is useful for prosthetic aortic heart valves, which typically have three leaflets joined at their adjacent edges at the upstanding commissure posts 30. Of course, the heart valves disclosed herein may be utilized in other implant locations, such as the pulmonary, mitral, or tricuspid annulus.

The lower wireform 28 is preferably metallic as well, but may be solid or a braided structure, as will be discussed. As seen in FIG. 1B, the lower wireform 28 has generally the same shape as the upper wireform 26 but with three truncated peaks 32 intermediate three cusp sections 34. The three cusp sections 34 closely parallel the cusps 31 of the upper wireform 26, but the truncated peaks 32 terminate well below the commissure posts 30.

In the illustrated embodiment, the peaks 32 of the lower wireform 28 are rotationally aligned with the commissure posts 30 of the upper wireform 26. In other embodiments, one or more of the peaks 32 is rotationally offset from the commissure posts 30. For example, in some embodiments, at least two peaks 32 are rotationally offset in the same direction. In some embodiments, at least a first peak is rotationally offset in an opposite direction as a second peak. In some embodiments, a first peak is rotationally offset by a different angular distance than a second peak.

Moreover, although the illustrated embodiment of the upper wireform 26 includes three commissure posts 30, in other embodiments, the upper wireform includes a different number of commissure posts, for example, two or four. In the illustrated embodiment, the number of peaks 32 on the lower wireform 28 matches the number of commissure posts 30 on the upper wireform 26: in this example, three of each. In other embodiments, the number of peaks is different than the number of commissure posts. For example, some embodiments include fewer peaks than commissure posts, for example, two peaks on a device with three commissure posts. Other embodiments include more peaks than commissures, for example, by replacing at least one of the peaks 32 with two peaks.

FIG. 3 is a view of the dual wireform assembly in a relaxed, unexpanded configuration showing exemplary dimensions. In a preferred embodiment, the truncated peaks 32 of the lower wireform 28 have an axial height $H_2$ of only about 10-30% of the axial height $H_1$ of commissure posts 30 of the upper wireform 26, and more preferably about 20%. The upper and lower wireforms 26, 28 define a circle of rotation at their inlet ends having a common diameter Di, with the two wireforms axially stacked and the lower wireform just below the upper wireform. Typically, heart valves are available in labeled sizes from 19 to up to 33 mm in 2-mm increments (e.g., 19 mm, 21 mm, 23 mm . . . ), and the diameter Di is between 19-33 mm, roughly corresponding to the labeled diameter of the finished valve 20. Other sizing schemes are also possible, for example, even millimeter sizing, and/or a sizing scheme implementing at least one different increment between sizes. The valves 20 disclosed herein have a functional size which equals the labeled size, whereas the valve becomes non-functional when expanded outward post-implant.

Figure 4:
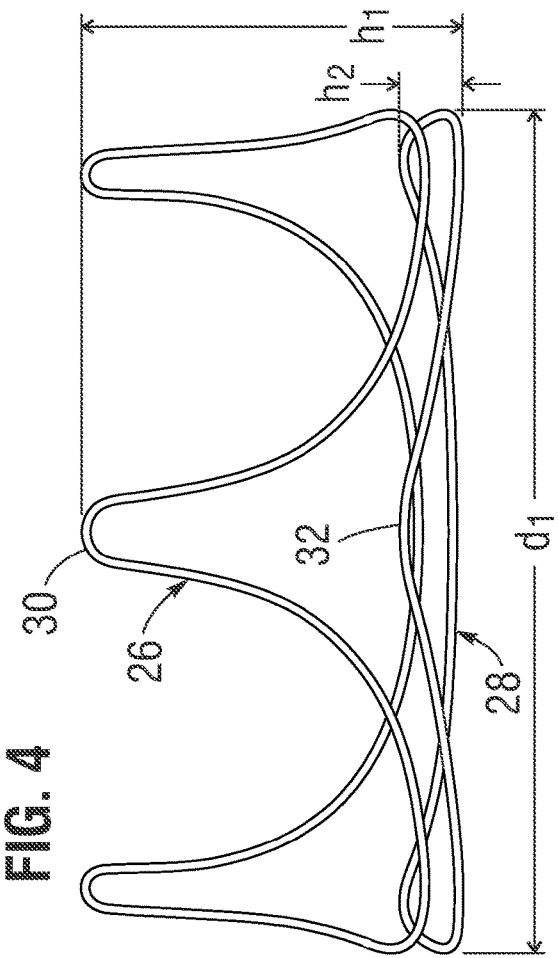
FIG. 4 is a view of the dual wireform assembly after expansion and showing altered dimensions.

FIG. 4 is a view of the dual wireform assembly after expansion and showing altered dimensions $d_1$, $h_1$, $h_2$. Namely, the dimension or diameter $d_1$ widens or increases by up to about 2-3 mm, preferably closer to about 2 mm for smaller valves and about 3 mm for larger valves. Recent publications report a drastically higher probability of annular rupture upon expanding the native annulus by more than 20% by area, such as when expanding a prosthetic heart valve therein. In light of this information, it is desirable to ensure that an expandable surgical valve expands by less than about 20% by area in some embodiments. Thus, for example, for a 19-mm valve a 20% increase in area corresponds to an increase in diameter of about 2 mm.

In other embodiments, the upper and lower wireforms 26, 28 do not have a common diameter. For example, in some embodiments, the lower wireform has a larger diameter than the upper wireform. In some of these embodiments, such a configuration permits nesting the upper wireform within the lower wireform, thereby reducing the overall height ($H_1$ and $h_1$) of the device. In some of these embodiments, the final diameters ($d_1$ in FIG. 4) of the upper and lower wireforms is different, while in other embodiments, the final diameters are substantially the same.

The heights $h_1$, $h_2$ of the upper and lower wireforms 26, 28, respectively, decrease when the wireforms expand. Because of the relatively high commissure posts 30 of the upper wireform 26, and their large capacity to expand outward toward the cusps 31, the height $h_1$ decreases a smaller proportion of the original height $H_1$ compared with $h_2/H_2$. However, since the lower wireform 28 has relatively shallower undulations between the peaks 32 and cusp sections 34 compared with the upper wireform 26, the reduced height $h_2$ is preferably less than about 50% of the original height $H_2$. More preferably, the lower wireform 28 flattens out to a great extent to more closely resemble a flat ring, thus presenting a relatively strong impediment to further expansion, such as with an expanding balloon during a valve-in-valve procedure. The expanded lower wireform 28 is shown with slight undulations, although it could be much flatter depending on the original height $H_2$ and the extent of expansion. Preferably the hoop strength of the lower wireform 28 increases to a magnitude sufficient to withstand balloon expansion from within after an expansion of between about 2-3 mm in diameter.

With reference back to FIG. 1D, further constructional details of the heart valve 20 include a plurality of inserts 36 which are located generally between the commissure posts 30 of the upper wireforms 26 and the peaks 32 of the lower wireforms 28 and help secure the leaflets 24 in place. One of the inserts 36 is shown covered with cloth in FIG. 1E. Additionally, a suture permeable sealing ring 38 surrounds the inlet end of the valve 20 and is used to secure the valve to the annulus. Typically, the sealing ring 38 comprises silicone, cloth or other such suture-permeable material, and is covered in fabric as seen in FIG. 1B.

Outer tabs 40 of adjacent leaflets 24 wrap around upper ends of commissure inserts 36 (preferably three) that project in an outflow direction along the flow axis 22. The commissure inserts 36 comprises elements separate from either the upper and lower wireforms 26, 28, and each has an inverted "Y" shape with a forked lower end 42 that generally conforms to a peak 30 of the lower wireform 28. Once covered in fabric, as illustrated for the one of the inserts shown in FIG. 1E, the inserts 36 are preferably positioned above the fabric-covered lower wireform 28 and secured to the leaflets 24 and fabric-covered upper wireform 26. Arcuate cusp edges of the leaflets 24 preferably extend between the cloth covered wireforms 26, 28 and are secured thereto with sutures.

Once assembled with the other valve components, the combination of the upper and lower wireforms 26, 28 presents a relatively dimensionally stable circumferential base to the valve 20, which is beneficial for typical surgical use. That is, primarily the lower wireform 28 provides good ring support to the cusp edges of the leaflets 24 and helps provide resistance to deformation of the valve during implantation. However, because of its undulating shape, the lower wireform 28 facilitates limited expansion of the valve 20.

During a valve-in-valve procedure, as the lower wireform 28 expands, the commissure posts 30 become spaced apart since the upper wireform 26 expands outward, which may lead to a loss of function of the valve 20. However, the valve becomes obsolete, having been replaced with a transcatheter valve, and so this loss of function is of no consequence. The wireform maintains the upstanding commissure posts of the expanded valve in roughly the same relative circumferential locations as when they were functional, which are intermediate the surrounding coronary ostia, and thus valve expansion will not end up blocking critical blood flow to the coronary arteries.

Figure 5:
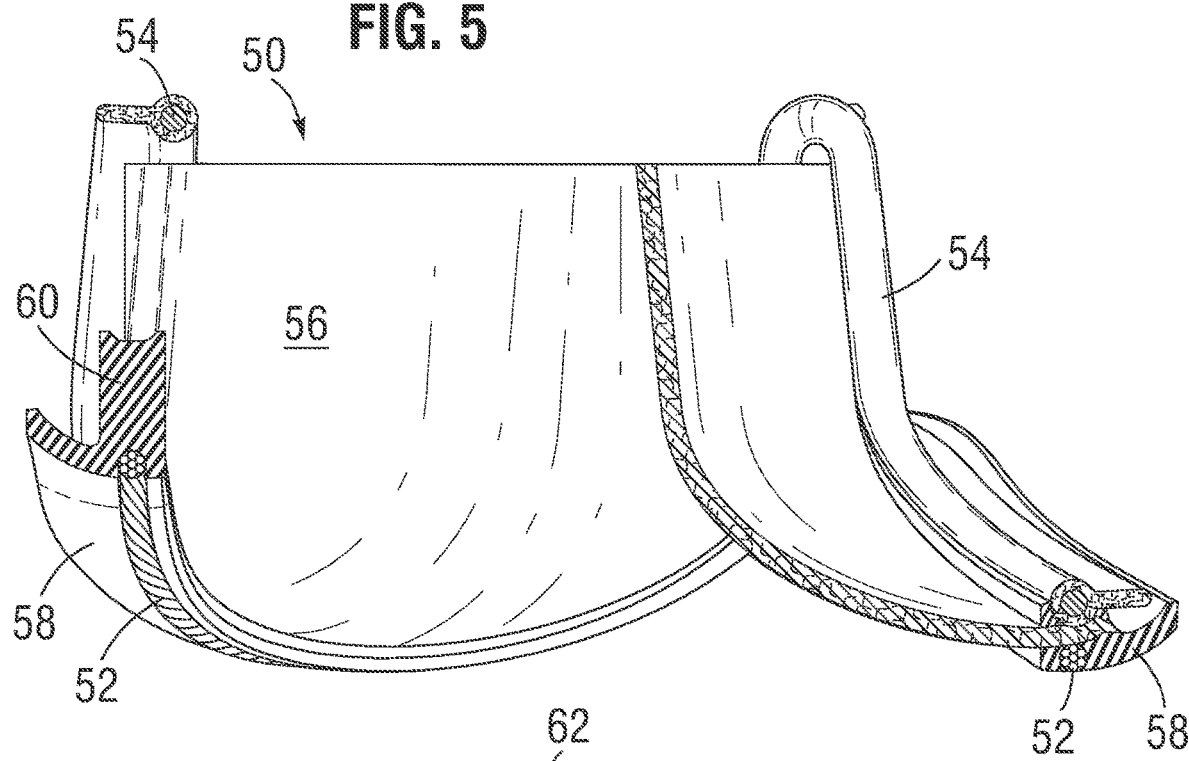
FIG. 5 is a sectional view through a heart valve having a dual wireform assembly where the lower wireform is a braided cable.

Another concept for limiting the expansion of prosthetic heart valves is shown in FIG. 5, which is a sectional view through an alternative heart valve 50 also having a dual wireform assembly where a lower wireform 52 is a braided cable. As before, the heart valve 50 has a cloth-covered upper wireform 54 and a plurality of leaflets 56 supported thereby. An outer sealing ring 58 includes a taller axial portion 60 at each of the commissure locations, which may be a molded silicone element or folded cloth or the like. Although not shown, commissure inserts such as those shown above at 36 may be utilized, and an outer cloth covering is not shown for clarity.

Figure 6A:
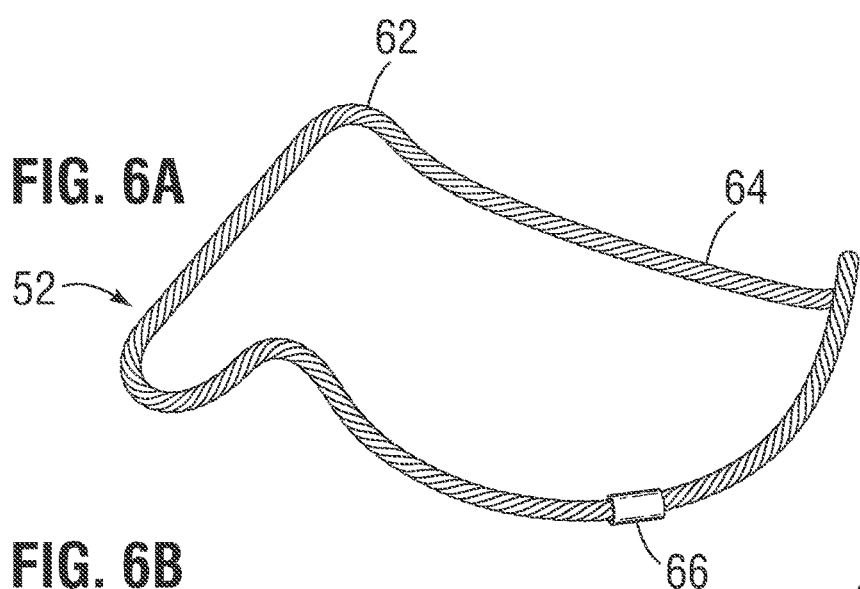
FIGS. 6A and 6B are perspective views of two different braided cable wireforms.
Figure 6B:
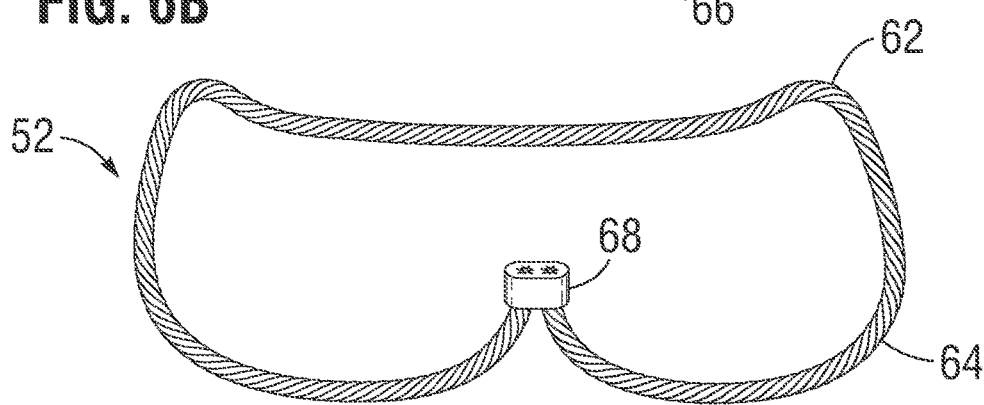

The lower wireform 52 is preferably shaped similarly to the lower wireform 28 described above, and is shown in two different embodiments in FIGS. 6A and 6B. Namely, the wireform 52 has an undulating shape with truncated peaks 62 in between arcuate cusp sections 64. The braided wireform 52 is preferably formed from an elongated braided cable or wire which is joined together at its free ends at either a weld 66 as seen in FIG. 6A, or at a crimp 68 such as seen in FIG. 6B. A weld 66 is typically used in the cusp sections 64, while a crimp 68 would be preferred at one of the peaks 62. Although not shown, the braided cable or wire is preferably held in the undulating shape as shown, such as with the use of a mandrel or other such manufacturing form, and heat set so that the shape is imparted to the cable. In a preferred embodiment, the braided wireform 52 is made of a plurality of braided strands of Nitinol that have been heat set. In this way, the wireform 52 provides a relatively stable peripheral base for the valve 50, but is also relatively flexible and permits post-implant expansion. In other embodiments, the braided wireform 52 comprises strands manufactured from another material, for example, stainless steel or cobalt-chromium. In other embodiments, the cable comprises a polymer, for example, ultra-high-molecular-weight polyethylene (UHMWPE, e.g., Spectra® (Honeywell, Morristown, N.J.) or Dyneema® (Heerlen, Netherlands) UHMWPE)) or polyaramid (e.g., Kevlar® (DuPont, Wilmington, Del.) or Twaron® (Teijin, Arnhem, Netherlands) aramid). Other embodiments of the cable comprise a composite including at least two of any of these materials. Some examples of the braided wireform 52 are manufactured in an annular shape, and consequently, do not include a weld or crimp. Examples of suitable manufacturing methods include weaving, knitting, or braiding.

In contrast to the lower wireform 28 described above, the braided wireform 52 is desirably embedded within the sealing ring 58, although the lower wireform 28 may also be embedded within the sealing ring. In one embodiment, the sealing ring 58 is a molded silicone element having the braided wireform 52 co-molded in an underside thereof. As mentioned, the assembly of the wireform 52 and sealing ring 58 may be covered with fabric and then joined to the upper wireform 54 and leaflets 56 via sutures. In FIG. 5, the cable 58 is disposed directly below the wireform 54. In other embodiments, the cable and wireform are radially offset. For example, as discussed above in connection with the lower wireform 28, the wireform 52 can nest within a cable with a larger diameter.

Figure 7A:
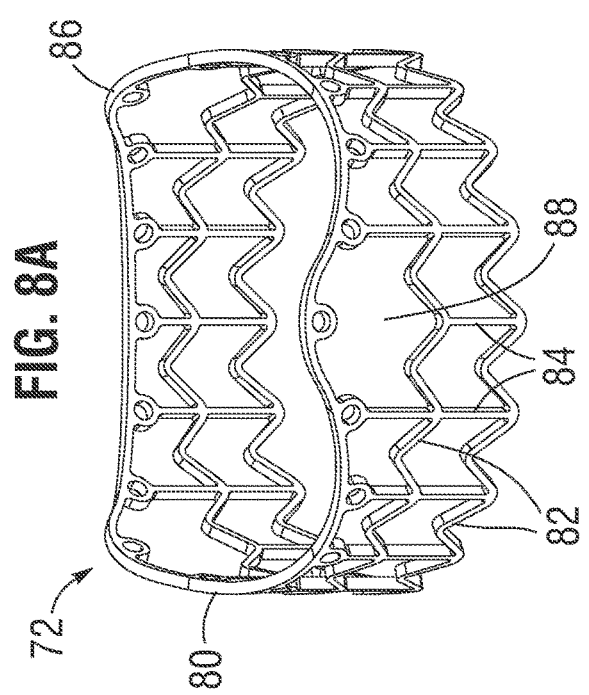
FIG. 7A is a partially cutaway view of another exemplary prosthetic heart valve having an expandable frame attached to an inflow end.
Figure 7B:
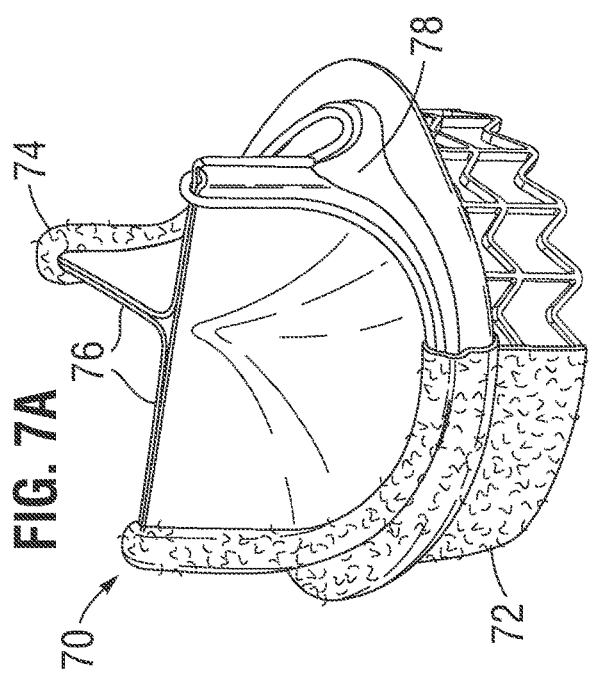
FIG. 7B is an elevational view of the heart valve where only the expandable frame is shown in solid lines.

FIG. 7A is a partially cutaway view of another exemplary prosthetic heart valve 70 having an expandable frame 72 attached to an inflow end, and FIG. 7B is an elevational view of the heart valve where only the expandable frame is shown in solid lines. As described above, the heart valve 70 includes an undulating wireform 74 that supports a plurality of flexible leaflets 76. Element number 78 refers to an inner support member which is adapted for post-implant expansion. That is, the support member 78 may comprise the lower wireforms 28, as described above, or may be a band structure which has at least one section adapted to expand from use of a dilatation balloon.

The addition of the expandable frame 72 creates a "hybrid" type of prosthetic heart valve in that the upper portion is constructed similar to a surgical valve, while the lower frame structure 72 is expandable to help in anchoring the valve in place. One specific commercial prosthetic heart valve that is constructed in this manner is one which is sold in conjunction with the Edwards Intuity® valve system from Edwards Lifesciences of Irvine, Calif. The Edwards Intuity® valve system comprises a "hybrid" valve incorporating essentially a surgical Perimount® valve, albeit one that is modified for post-implant expansion, and a stainless steel lower frame structure or skirt stent.

Figure 8A:
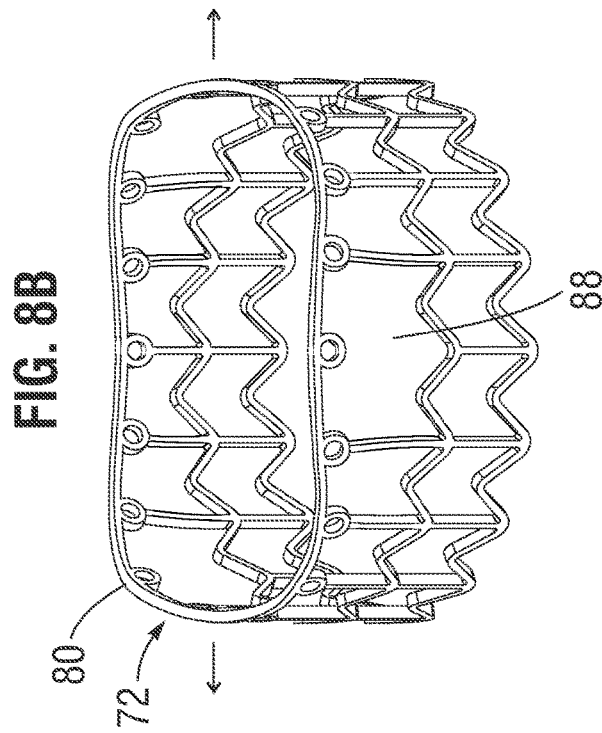
FIG. 8A is a perspective view of the expandable frame isolated from the heart valve.
Figure 8B:
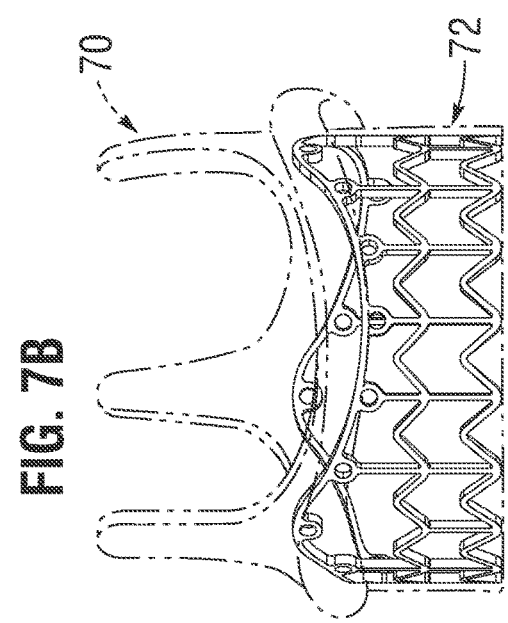
FIG. 8B is a perspective view of the expandable frame after expansion.

FIG. 8A is a perspective view of the expandable frame 72 isolated from the heart valve 70, and FIG. 8B is a perspective view of the expandable frame after expansion. The frame 72 includes an upper undulating strut 80 that extends around the entire periphery of the frame and above a plurality of generally V-shaped circumferential struts 82 extending between axial struts 84. The undulating strut 80 includes three peaks 86 that generally conform to the undulating shape of the inflow end of the heart valve 70, as best seen in FIG. 7B. In other words, the three peaks 86 correspond to the three commissures 74 of the valve. An absence of the vertical struts 84 immediately below each of the three peaks 86 creates a space or void 88. Due to the upper curvature of the peaks 86, this permits the undulating strut 80 to expand outward such as seen in FIG. 8B upon application of a dilatory force within the hybrid prosthetic valve.

In one embodiment, the aforementioned inner support member 78 may be omitted completely from the prosthetic valve 70 with the undulating strut 80 providing support to the base of the valve and the leaflets. For example, the undulating strut 80 may be positioned approximately the same place as the braided wireform 52 seen in FIG. 5. To prevent premature expansion of the undulating strut 80 at the time of implant of the valve 70, a biodegradable band may be assembled around the inflow end of the surgical valve 70. Such a biodegradable band is seen in FIG. 15 of U.S. Pat. No. 9,375,310 to Chung, et al., the contents of which are expressly incorporated herein by reference, and serves to prevent expansion of the upper end of the frame 72 at the time of initial implant of the valve 70. Subsequently, years later, if the valve 70 malfunctions, the biodegradable band has dissolved and a dilatation balloon can easily expand the undulating strut 80.

While certain principles have been described with reference to particular embodiments, it will understood that various changes and additional variations may be made and equivalents may be substituted for elements thereof without departing from the scope of the disclosure. In addition, many modifications may be made to adapt a particular situation or device to the teachings without departing from the essential scope thereof. Therefore, it is intended that the disclosure not be limited to the particular embodiments disclosed herein, but will include all embodiments falling within the scope of the appended claims.

What is claimed is:

1. A prosthetic heart valve adapted for post-implant expansion and having an inflow end and an outflow end, comprising:
   an upper wireform undulating around a central axis with three upstanding commissure posts extending in an outflow direction alternating with three arcuate inflow cusps, and a fabric covering around the entire upper wireform;
   a lower wireform undulating around a central axis with three truncated peaks extending in an outflow direction alternating with three arcuate inflow cusp sections, and a fabric covering around the entire lower wireform, the lower wireform being positioned axially below the upper wireform with the three truncated peaks being aligned under three upstanding commissure posts, and the wherein the truncated peaks have an axial height of between about 10-30% of the commissure posts of the upper wireform;
   three flexible leaflets having outer arcuate cusp edges attached between the inflow cusps of the upper wireform and the inflow cusp sections of the lower wireform and outer tabs that extend outward between the commissure posts of the upper wireform and the truncated peaks of the lower wireform and are secured to the fabric covering around the upper wireform, the flexible leaflets being configured to ensure one-way blood flow through the heart valve, and
   wherein the inflow cusps of the upper wireform and the inflow cusp sections of the lower wireform together define an implant circumference having a first diameter, and wherein the upper and lower wireforms permit expansion of the heart valve from the first diameter to a second diameter no greater than 3 mm larger than the first diameter upon application of an outward dilatory force from within the heart valve substantially larger than forces associated with normal physiological cycling, and wherein the lower wireform has a shallow undulating shape that flattens out and prevents expansion of the heart valve beyond the second diameter.

2. The prosthetic heart valve of claim 1, further including three fabric-covered inserts located above the truncated peaks of the lower wireform that extend upward radially outward of the commissure posts of the upper wireform, the leaflet tabs being also secured to the inserts.

3. The prosthetic heart valve of claim 2, wherein a lower end of each insert has an inverted Y-shape that closely matches a shape of the truncated peaks of the lower wireform.

4. The prosthetic heart valve of claim 1, further including an annular sealing ring disposed outward of the inflow cusp sections of the lower wireform and being secured thereto, the annular sealing ring being suture permeable.

5. The prosthetic heart valve of claim 4, wherein the lower wireform is embedded within the sealing ring.

6. The prosthetic heart valve of claim 1, wherein the lower wireform comprises a solid wire.

7. The prosthetic heart valve of claim 1, wherein the lower wireform comprises a braided cable.

8. The prosthetic heart valve of claim 1, further including an expandable frame attached to an inflow end of the heart valve and projecting therefrom in the inflow direction, the expandable frame having an upper undulating strut that extends around an entire periphery thereof and a plurality of lower struts, the undulating strut having a shape that closely follows the shape of the undulating lower wireform, wherein there are no lower struts below three peaks of the undulating strut to permit flattening out of the undulating strut upon application of an outward dilatory force from within the heart valve substantially larger than forces associated with normal physiological cycling.

9. A prosthetic heart valve adapted for post-implant expansion and having an inflow end and an outflow end, comprising:
   an upper wireform undulating around a central axis with three upstanding commissure posts extending in an outflow direction alternating with three arcuate inflow cusps, and a fabric covering around the entire upper wireform;
   an annular sealing ring disposed outward of the inflow cusps of the upper wireform and being secured thereto, the annular sealing ring being suture permeable;

a lower wireform comprising a braided cable undulating around the central axis with three truncated peaks extending in an outflow direction alternating with three arcuate inflow cusp sections, the braided cable being embedded within the sealing ring and the three truncated peaks being aligned under the three upstanding commissure posts of the upper wireform;

three flexible leaflets having outer arcuate cusp edges attached between the inflow cusps of the upper wireform and the sealing ring and having outer tabs that extend outward between the commissure posts of the upper wireform and are secured to the fabric covering around the upper wireform, the flexible leaflets being configured to ensure one-way blood flow through the heart valve, and wherein the inflow cusps of the upper wireform and the inflow cusp sections of the lower wireform together define an implant circumference having a first diameter, and wherein the upper wireform and lower wireform permit expansion of the heart valve from the first diameter to a second diameter no greater than 3 mm larger than the first diameter upon application of an outward dilatory force from within the heart valve substantially larger than forces associated with normal physiological cycling, and wherein the lower wireform has a shallow undulating shape that flattens out and prevents expansion of the heart valve beyond the second diameter.

10. The prosthetic heart valve of claim 9, further including three fabric-covered inserts located above the truncated peaks of the lower wireform that extend upward radially outward of the commissure posts of the upper wireform, the leaflet tabs being also secured to the inserts.

11. The prosthetic heart valve of claim 10, wherein a lower end of each insert has an inverted Y-shape that closely matches a shape of the truncated peaks of the lower wireform.

12. The prosthetic heart valve of claim 9, wherein the braided cable is joined together at free ends at a weld in one of the cusp sections.

13. The prosthetic heart valve of claim 9, wherein the braided cable is joined together at free ends at a crimp at one of the truncated peaks.

14. The prosthetic heart valve of claim 9, further including an expandable frame attached to an inflow end of the heart valve and projecting therefrom in the inflow direction, the expandable frame having an upper undulating strut that extends around an entire periphery thereof and a plurality of lower struts, the undulating strut having a shape that closely follows the shape of the undulating lower wireform, wherein there are no lower struts below three peaks of the undulating strut to permit flattening out of the undulating strut upon application of an outward dilatory force from within the heart valve substantially larger than forces associated with normal physiological cycling.

15. The prosthetic heart valve of claim 9, wherein the braided cable is made of braided strands of Nitinol.

16. The prosthetic heart valve of claim 15, wherein the braided cable is heat set into the undulating shape.

17. The prosthetic heart valve of claim 9, wherein the braided cable is made of braided strands of stainless steel or cobalt-chromium.

18. The prosthetic heart valve of claim 9, wherein the braided cable is made of braided strands of polymer.

19. The prosthetic heart valve of claim 9, wherein the sealing ring is a molded silicone element and the lower wireform is co-molded in an underside thereof.

20. The prosthetic heart valve of claim 19, wherein the lower wireform and sealing ring are covered with fabric and joined to the upper wireform and leaflets via sutures.

* * * * *